United States Patent [19]

Teranishi

[11] Patent Number: Plant 6,315

[45] Date of Patent: Oct. 4, 1988

[54] MADAME VIOLET ROSE PLANT

[75] Inventor: Kikuo Teranishi, Itami, Japan

[73] Assignee: Carlton Rose Nurseries, Inc., Carlton, Oreg.

[21] Appl. No.: 928,895

[22] Filed: Nov. 10, 1986

[51] Int. Cl.[4] ..... A01H 5/00

[52] U.S. Cl. ..... Plt./11

[58] Field of Search ..... Plt. 11

*Primary Examiner*—James R. Feyrer

*Attorney, Agent, or Firm*—Chernoff, Vilhauer, McClung & Stenzel

[57] ABSTRACT

A vigorous rose plant of the hybrid tea class obtained as a seedling from a seed parent entitled "Lady X" and a pollen parent entitled "Sterling Silver" provide abundant long-lasting delicate violet blooms which maintain their true color from bud through leaf drop, on a continuous basis when grown in a greenhouse.

1 Drawing Sheet

BACKGROUND AND SUMMARY OF THE INVENTION

The present invention relates to a new and distinct variety of hybrid tea rose plant, a seedling resulting from a definite effort to produce an improvement in this class of rose. The object of the present invention is to provide a hardy rose plant of the hybrid tea class which is capable of freely yielding quality cut flowers under greenhouse conditions.

The primary features of this new variety which connotes its distinctive advance over previously existing types are its vigorous growth, its delicate violet color, its ability to continuously yield cut flowers which maintain true color after being cut, from bud through petal drop under greenhouse and outdoor conditions.

The variety of rose plant of the present invention was obtained at Itami, Japan as a seedling from a seed parent entitled "Lady X" and a pollen parent entitled "Sterling Silver." The crossing was made during 1972, the sowing during 1973 and the first flower appeared during March, 1973.

Asexual reproduction of this new and distinct variety shows that its unique characteristics come true to form and is established and transmitted through succeeding propagations through grafting and by budding.

BRIEF DESCRIPTION OF DRAWINGS

In the accompanying photographs typical specimens of the vegetative growth and flowers of the new variety are shown in different stages of development and are depicted in color as nearly true as is reasonably possible to make the same in color illustrations of this character:

FIG. 1 shows a developing flower bud.

FIG. 2 shows a flower bud at cutting stage with sepals down.

FIG. 3 shows a three-day-old developing flower.

FIG. 4 shows flower petals with the outside of the pedal shown above and the inside of the petal shown below.

FIG. 5 shows a fully developed flower.

FIG. 6 shows a flower with the petals removed exposing the anthers and stamens.

FIG. 7 shows a flower with the petals, stamens and anthers removed exposing the pistils.

FIG. 8 shows a flower with the petals removed cut in cross section exposing the receptacle stamens and pistils.

FIG. 9 shows a section of the flower stem at the point of branching.

FIG. 10 shows the upper side of a compound leaf.

FIG. 11 shows the underside of a compound leaf.

FIG. 12 shows a flowering stem with the leaves and flowers removed.

FIG. 13 shows five flowers in a vase showing normal form and color.

DETAILED DESCRIPTION OF THE DISCLOSURE

The following description was made during July, 1986 of the rose plants of the new and distinct variety growing in a greenhouse at Carlton, Oreg. Color designations are to Royal Horticultural Society Colour Chart.

Flower:

*Flowers borne.*—Singly and three to a stem on long, strong stems.

*Quantity of bloom.*—Abundant in greenhouse.

*Continuity.*—Continuous.

*Fragrance.*—Slight.

*Bud.*—Peduncle: Medium length; medium weight; erect; medium green; almost smooth; few prickles, yellow. Before calyx breaks: Size: Medium. Form: Medium pointed without foliaceous appendages on the surface of the bud; without foliaceous parts extending beyond the tip of the bud. As calyx breaks: Color: Purple Group 78-C. As first petal opens: Size: Medium. Form: Long pointed. Color: Outside: Purple-Violet Group 80-C. Inside: Purple-Violet Group 81-D. Opening: It does open up well.

*Bloom.*—Size when fully open: Medium: 3 inches to 5 inches. Petalage: Double; from 29 to 33 petals; arranged regularly. Form: High centered at first; becoming open, high centered; petals remaining at first tightly rolled inward; becoming later at maturity loosely rolled outward.

*Petals.*—Medium; With inside satiny; outside satiny.

*Shape.*—Outer: Obovate; with base flat. Intermediate: Obovate; with one tooth. Inner: Obovate; irregular with one notch.

*Color.*—Color of newly opened flower: Outer petal: Outside surface: Purple Group 76-B. Inside surface: Red-Purple Group 69-C. Intermediate petal: Outside surface: Purple Group 76-C. Inside surface: Purple Group 76-D. Inner petal: Outside surface: Red-Purple Group 69-C. Inside surface: Red-Purple Group 69-D. Color of flower 3 days after opening: Outer petal: Outside surface: Red-Purple Group 69-D. Inside surface: Purple Group 76-D. Inner petal: Outside surface; Red-Purple Group 69-C. Inside surface: Red-Purple Group 69-D.

*General color effect.*—Newly opened flower: Almost a uniform color overall. Flowers three days open: Slightly darker color in center gradually fading toward outside.

*Behavior.*—Drop off cleanly.

*Flower longevity.*—Cut flowers grown in greenhouse kept at living room temperature, 10 days during June. On bush outdoors, 10–13 days in May; cut roses grown outdoors kept at living room temperature, 8 days in May.

Reproductive organs:

*Stamens.*—Medium number; arranged regularly about pistils; tucked in receptacle.

*Filaments.*—Many; most with anthers; medium in length. Color: Yellow-Orange Group 19-C.

*Anthers.*—All open at once; medium size. Color: Yellow-Orange Group 20-B; seldom an anther fused with a petaloid. Pollen: Abundant; yellow. Pistils: Many. Styles: Even; medium length; thin; bunched. Stigma: Yellow. Ovaries: All enclosed. Hips: Oblong: pear shaped; very smooth; thick, fleshy walls; orange. Sepals: Permanent; moderately long; spear-shaped; recurved. Seeds: Many; large.

Plant:

*Foliage.*—Leaves: Compound of 3 and 5 leaflets; moderately abundant; moderately large size; moderately heavy leathery.

*Leaflet.*—Shape: Lanceolate; apex acuminate; base round; margin simply serrate. Color: Mature upper surface: Green Group 136-A. Mature under surface: Grey Green Group 191-B. Young upper surface: Green Group 137-A. Young under surface: Grey-Green Group 191-B.

*Rachis.*—Medium. Upper side: Grooved. Under side: Sparsley thorny.

*Stipules.*—Moderately long; with medium points; turning out at an angle of less than 90 degrees.

*Disease.*—Rèsistance comparable to the average variety growing under the same cultural conditions.

Growth:

*Habit.*—Upright; much branched.

*Growth.*—Vigorous.

*Canes.*—Moderately heavy.

*Main stems.*—Dull. Color: Yellow-Green Group 146-B. Prickles: Several. Color: Grey-Brown Group 199-B. Hairs: None.

*Branches.*—Dull. Color: 137-C. Prickles: Several. Color: Grey-Green Group 197-B. Hairs: None.

*New shoots.*—Dull. Color: Green Group 143-C. Prickles: Few. Color: Grey-Orange Group 174-B. Hairs: None.

What is claimed is:

1. A new and distinct variety of rose plant of the hybrid tea class obtained as a seedling from a seed parent entitled "Lady X" and pollen parent entitled "Sterling Silver," characterized by its vigorous growth, its delicate violet color, its ability to yield on a continuous basis in a greenhouse flowers which maintain true color after being cut from bud through petal drop, and its ability to grow outdoors, substantially as shown and described.

* * * * *

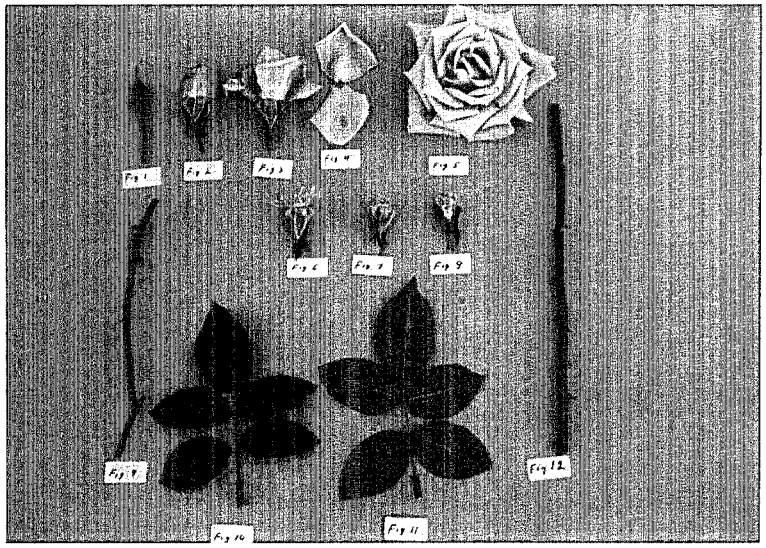
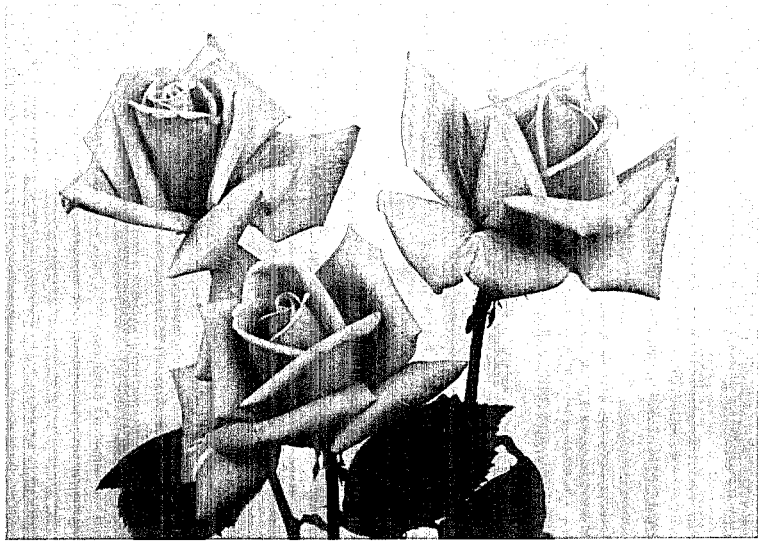
FIG. 13